US00PP33353P2

(12) United States Plant Patent
Bradford et al.

(10) Patent No.: US PP33,353 P2
(45) Date of Patent: Aug. 17, 2021

(54) PLUM TREE NAMED 'PLUMRED V'

(50) Latin Name: *Prunus salicina*
Varietal Denomination: Plumred V

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 16/974,338

(22) Filed: Jan. 4, 2021

(51) Int. Cl.
*A01H 5/08* (2018.01)
*A01H 6/74* (2018.01)

(52) U.S. Cl.
USPC ..... Plt./184

(58) Field of Classification Search
USPC ..... Plt./156, 184
See application file for complete search history.

(56) References Cited

U.S. PATENT DOCUMENTS

PP23,718 P3 7/2013 Bradford

*Primary Examiner* — Susan McCormick Ewoldt
*Assistant Examiner* — Karen M Redden

(57) ABSTRACT

The present invention relates to a plum tree, *Prunus salicina*, and more particularly to a new and distinct variety broadly characterized by a-medium size, vigorous, hardy, and productive tree. Being self-unfruitful, the present variety requires cross pollination from an apricot, interspecific, or plum that blooms during the mid season, such as 'Santa Rosa' plum tree (unpatented). The present variety produces a heavy amount of flowers that produce an abundance of pollen to entice good bee activity to facilitate pollination. The fruit matures under the ecological conditions described during mid June, with first picking on Jun. 10, 2020. The fruit is uniformly medium in size, dark red in skin color, full deep red in flesh color, clingstone in type, globose in shape, firm in texture, juicy, very sweet, and very good in flavor.

1 Drawing Sheet

Botanical classification: *Prunus salicina.*
Varietal denomination: 'PLUMRED V'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits. The present invention relates to a new and distinct variety of plum tree which has been denominated varietally as 'Plumred V'.

During a typical blooming season we isolate as seed parents both individual and groups of different plum and interspecific trees by covering them with screen houses. A hive of bees is placed inside each such house, and bouquets to provide pollen from different plum, apricot, and interspecific hybrid trees are placed in buckets near the trees approximately every two days for the duration of the bloom. During 2012 one such house containing '39P1184' plum tree (unpatented) was crossed by us in this manner. To pollinate this plum tree, we selected bouquets from several sources of plum trees without keeping specific written details. Upon reaching maturity the fruit from this interspecific tree was harvested, and the seeds were removed, cracked, stratified and germinated as a group with the label "H19". They were grown as seedlings on their own root in our greenhouse and upon reaching dormancy transplanted to a cultivated area of our experimental orchard located near Le Grand, Calif. in Merced County (San Joaquin Valley). During the summer of 2015 the claimed variety was selected by us as a single plant from the group of seedlings described above. Subsequent to origination of the present variety of plum tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent '39P1184' plum tree (unpatented), by being self-unfruitful and by producing fruit that is very dark red in skin and flesh color, firm and sweet, but is quite distinguished therefrom by producing fruit that is much larger in size and that ripens about five weeks earlier.

The present variety is most similar to 'Blackred VI' interspecific tree (U.S. Plant Pat. No. 23,718), by being self-unfruitful and by producing fruit that is medium in size, firm in texture, sweet, very dark red in skin color, full deep red in flesh color, and clingstone in type, but is distinguished therefrom by blooming in the mid instead of early season and by producing fruit that is globose instead of oblate in shape, and that matures about 10 days earlier.

SUMMARY OF VARIETY

The present plum variety is characterized by a medium size, vigorous, hardy, and productive tree. Being self-unfruitful, the present variety requires cross pollination from an apricot, interspecific, or plum that blooms during the mid season, such as 'Santa Rosa' plum tree (unpatented). The present variety produces a heavy amount of flowers that produce an abundance of pollen to entice good bee activity to facilitate pollination. The fruit matures under the ecological conditions described during mid June, with first picking on Jun. 10, 2020. The fruit is uniformly medium in size, dark red in skin color, full deep red in flesh color, clingstone in type, globose in shape, firm in texture, juicy, very sweet, and very good in flavor.

DRAWING

The accompanying photograph consists of four whole fruits positioned to display the characteristics of the skin color and form, one divided fruit to reveal the flesh and stone, a tip shoot growth, typical leaves, and two insets depicting the flower buds and blossoms as they appeared on the tree during the blooming season.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif. The fruit description was developed at the state of firm ripe on Jun. 22, 2020, on the original tree during its eighth growing season. The flower and bud descriptions were developed during the previous blooming season. All major color code designations are by reference to the Inter-Society Color Council, National Bureau of Standards. Common color names are also used occasionally.

PARENTAGE

Seed parent: 39P1184 (unpatented) plum tree.
Pollen parent: Unknown plum.

TREE

Size: Medium, reaching and maintaining a height of 10' [3.05 m.] and a spread of 7' [2.13 m.] after eight growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Pruned to a vase form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-unfruitful, requiring cross pollination by a suitable mid seasonal blooming apricot, interspecific, or plum, such as 'Santa Rosa' plum tree (unpatented).

Bearing: Regular bearer, weather dependent, no crop failures observed as of yet.

Trunk:

- *Size*.—Stocky, reaching a maximum diameter of 6" [152.4 mm.] after the eighth growing season.
- *Texture*.—Medium to shaggy.
- *Bark color*.—A Light grayish brown [60. l.gy.Br] and Brownish gray [64. brGy] variegation with Dark grayish brown [62. d.gy.Br] crevices present.
- *Lenticels*.—Approximate Number Per Square Inch: 10. Color: Strong brown [55. s.Br]. Average Size: ¼" [6.4 mm.] in length. The width is typically one fourth as much as the length. Shape: Elongated.

Branches:

- *Size*.—Medium, scaffold diameter is 2¼" [57.2 mm.] measured 12" above the crotch, limb diameter is 1½" [38.1 mm.] measured 12" above the first fork.
- *Texture*.—Medium to shaggy.
- *Color*.—1st Year Wood Topside: Grayish red [19. gy.R]. 1st Year Wood Underside: Brilliant yellow green [116. brill.YG]. Older Wood: A Moderate yellowish brown [77. m.yBr] and Dark yellowish brown [78. d.yBr] variegation with Strong yellowish brown [74. s.yBr] crevices present.
- *Lenticels*.—Number Per Square Inch: About 22 on second year wood. Color: Strong yellowish brown [74. s.yBr]. Average Size: Small, 1/32" [0.8 mm.] in length. The width is typically one fourth as much as the length. Shape: Elongated.

Leaves:

- *Size*.—Medium to small. Average Length: 3¼" [82.6 mm.]. Average Width: 1¾" [44.5 mm.].
- *Arrangement*.—Alternate.
- *Thickness*.—Medium.
- *Form*.—Elliptical.
- *Apex*.—Acuminate.
- *Base*.—Acute with an average base angle of 75 degrees.
- *Surface*.—Smooth.
- *Color*.—Dorsal Surface: Moderate olive green [125. m.OlG]. Ventral Surface: Moderate yellow green [120. m.YG].
- *Margin*.—Finely serrate.
- *Venation*.—Pinnately net veined.
- *Petiole*.—Average Length: ½" [12.7 mm.]. Average Thickness: 1/16" [1.6 mm.]. Color: Vivid yellow green [115. v.YG].
- *Stipules*.—Number: Mostly 2 per leaf, up to 6 per growing tip. Average Length: ¼" [6.4 mm.]. Color: Moderate yellow green [120. m.YG] becoming Dark grayish yellow [91. d.gy.Y] with age.
- *Glands*.—Number: Mostly 2 per leaf. Position: Alternate, positioned at the intersection of the petiole and base of leaf blade. Form: Globose. Size: Small to medium, 1/32" [0.8 mm.] in diameter. Color: Light yellow green [119. l.YG] becoming Moderate reddish brown [43. m.rBr] in the center with age. Leaf buds: Pointed.

Flower buds:

- *Hardiness*.—Hardy, with respect to central California blooming season.
- *Diameter*.—Typically 3/16" [4.8 mm.] 1 week before bloom.
- *Length*.—Typically ⅜" [9.5 mm.] 1 week before bloom.
- *Form*.—Free, not touching.
- *Surface*.—Slightly pubescent.
- *Tip color*.—White [263. White].

Flowers: Perfect, complete, perigynous, usually a single pistil, about thirty stamens, five sepals and petal locations alternately positioned.

- *Average flower diameter*.—1¼" [31.8 mm.].
- *Average flower depth*.—⅜" [9.5 mm.] when fully open.

*Number of petals*.—Five, no double blossoms observed.
*Petal shape*.—Oval.
*Petal margin*.—Entire, quite wavy.
*Petal arrangement*.—Not overlapping when fully open.
*Average petal diameter*.—9/16" [14.3 mm.].
Average petal length.—11/16" [17.5 mm.].
*Petal apex*.—Rounded.
*Petal base*.—Obtuse.
*Petal color*.—White [263. White] on both sides.
*Anther color*.—Moderate orange yellow [71. m.OY].
*Pollen production*.—Strong, enticing to bees.
*Stigma color*.—Vivid greenish yellow [97. v.gY].
*Stigma position*.—Located about even with the average anther position.
*Stamen position*.—Typically located about 1/32" [0.8 mm] below the petals.
*Sepal color*.—Strong yellow green [117. s.YG] on the outside, Brilliant yellow green [116. brill.YG] on the inside.
*Sepal outer surface*.—Slightly pubescent.
*Sepal length*.—3/16" [4.8 mm.].
*Sepal width*.—1/8" [3.2 mm.].
*Sepal apex*.—Rounded to elliptical to match the width and length.
*Sepal margin*.—Fairly smooth.
*Average pistil length*.—11/16" [17.5 mm.].
*Average stamen length*.—5/8" [15.9 mm.].
*Ovary*.—Smooth.
*Fragrance*.—Moderate.
*Pollen production*.—Strong, bee enticing.
*Bloom density*.—Heavy.
*Number per cluster*.—1 to 5, mostly 2.
*Blooming period*.—Medium, with 'Santa Rosa' plum (unpatented).
*Onset of bloom*.—One percent on Feb. 21, 2020.
*Date of full bloom*.—Mar. 4, 2020.
*Duration of bloom*.—One to two weeks, dependent on ambient temperature.

FRUIT

Maturity when described: Firm ripe, Jun. 22, 2020.
Date of first picking: Jun. 10, 2020.
Date of last picking: Jun. 20, 2020.
Size: Uniform, medium.
*Average diameter axially*.—2½" [63.5 mm.].
*Average diameter across cheek plane*.—2½" [63.5 mm.].
*Average diameter across suture plane*.—2½" [63.5 mm.].
*Typical weight*.—5.1 ounces [145 grams].
Form: Uniform, globose, symmetrical.
*Longitudinal section form*.—Round.
*Axial view form*.—Round.
Suture: A shallow trough extending from the base just to the pistil point.
Ventral surface: Rounded, very slightly lipped on both sides.
Lips: Fairly equal.
Cavity: Flaring.
*Depth*.—3/8" [9.5 mm.].
*Breadth*.—7/8" [22.2 mm.].
*Stem markings*.—Usually absent, Moderate yellow [87. m.Y] when present.
Base: Truncate, somewhat cordate if viewed parallel to the suture.
Apex: Rounded.
Pistil point: An inconspicuous Light yellowish brown [76. l.yBr] dot.
Stem: Medium.
*Average length*.—7/16" [11.1 mm.].
*Average width*.—1/16" [1.6 mm.].
Skin:
*Thickness*.—Medium.
*Surface*.—Smooth.
*Tenacity*.—Tenacious to the flesh.
*Astringency*.—Moderate.
*Tendency to crack*.—None observed.
*Color*.—Very deep purplish red [257. v.deep pR] over a Dark red [16. d.R] background with heavy, but very fine, Light yellowish brown [76. l.yBr] freckling throughout.
Flesh:
*Color*.—Very deep red [14. v.deep R] close to the skin smoothly blending to Strong red [12. s.R] toward the stone with Moderate red [15. m.R] fibers throughout.
*Surface of pit cavity*.—Covered with Very dark red [17. v.d.R] fibers when twisted from the stone.
*Amygdalin*.—Moderate.
*Juice*.—Abundant, rich.
*Texture*.—Firm, tough, meaty.
*Fibers*.—Abundant, fine.
*Ripens*.—Fairly even.
*Flavor*.—A very tasty blend of acid and sugar, typically 18-19 brix.
*Aroma*.—Very slight.
*Eating quality*.—Very good.

STONE

Type: Clingstone.
Form: Obovate.
Hilum: Narrow.
Base: Cordate.
Apex: Obtuse.
Tip: Sharp, about 1/16" [1.6 mm.] in length.
Sides: Mostly equal.
Surface: Fairly smooth with rounded ridges toward the base.
External color of stone: Light orange yellow [70. l.OY].
Pit wall color when cracked: Light orange yellow [70. l.OY].
Cavity surface color: Brownish orange [54. brO].
Average pit wall thickness: 1/16" [1.6 mm.].
Average length: 1" [25.4 mm.].
Average width: 13/16" [20.6 mm.].
Average breadth: 1/4" [6.4 mm.].
Tendency to split: None observed.
Kernel:
*Form*.—Oval.
*Skin color*.—Pale orange yellow [73. p.OY].
*Pellicle color*.—Dark yellowish brown [78. d.yBr].
*Vein color*.—Light brown [57. l.Br].
*Taste*.—Bitter.
*Viable*.—Yes.
*Average length*.—5/8" [15.9 mm.].
*Average width*.—3/8" [9.5 mm.].
*Amygdalin*.—Moderate.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, *Prunus salicina*, substantially as illustrated and described, that is most similar to 'Blackred VI' interspecific tree (U.S. Plant Pat. No. 23,718), by being self-unfruitful and by producing fruit that is medium in size, firm in texture, sweet, very dark red in skin color, full deep red in flesh color, and clingstone in type, but is distinguished therefrom by blooming in the mid instead of early season and by producing fruit that is globose instead of oblate in shape, and that matures about 10 days earlier.

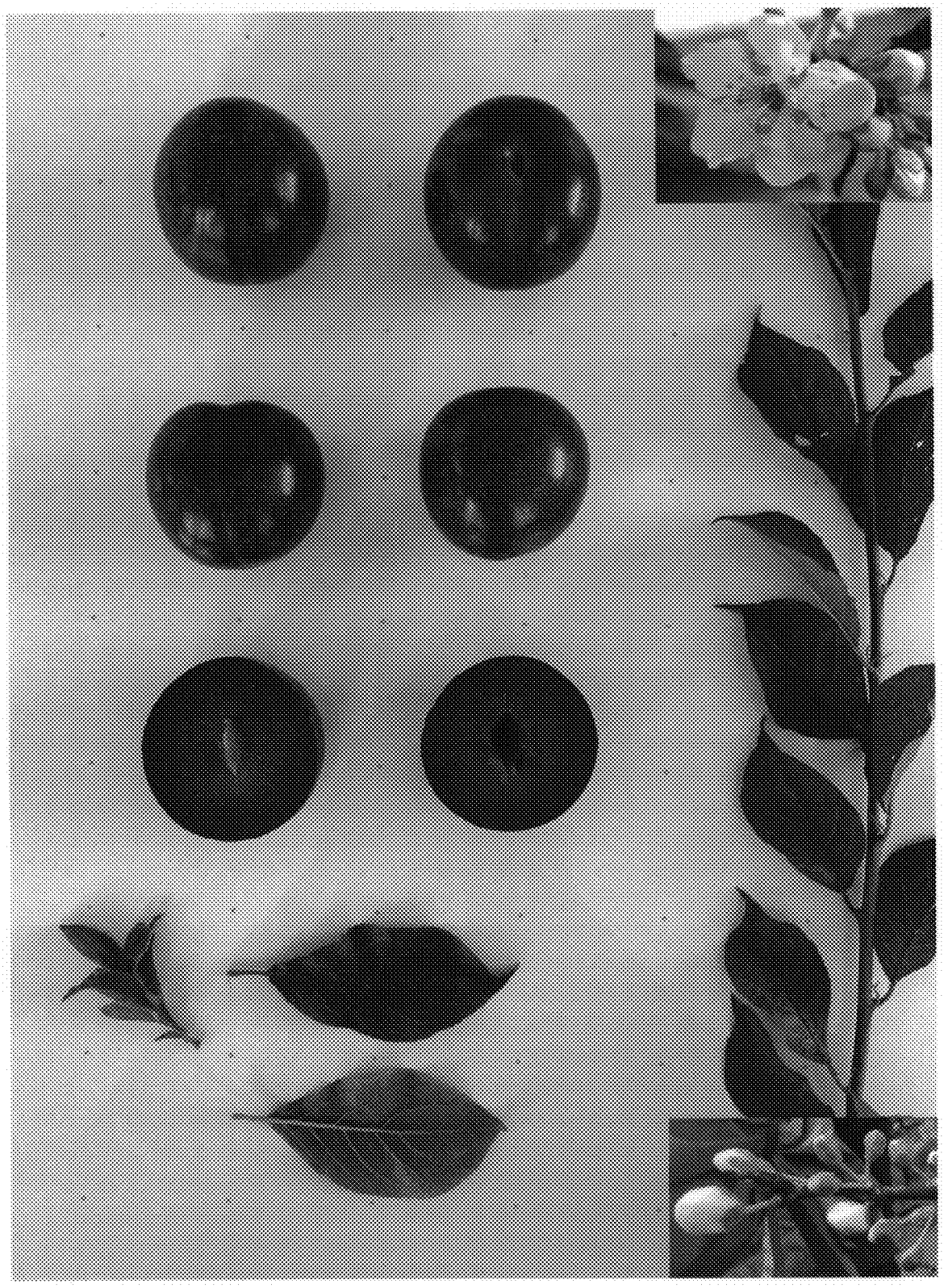

* * * * *